(12) United States Patent  
Liu

(10) Patent No.: US 9,320,296 B2
(45) Date of Patent: Apr. 26, 2016

(54) METHOD OF MAKING FERMENTED TURTLE SHELL POWDER

(71) Applicant: Canhui Liu, Lutz, FL (US)

(72) Inventor: Canhui Liu, Lutz, FL (US)

( * ) Notice: Subject to any disclaimer, the term of this patent is extended or adjusted under 35 U.S.C. 154(b) by 80 days.

(21) Appl. No.: 14/187,779

(22) Filed: Feb. 24, 2014

(65) Prior Publication Data

US 2015/0237904 A1   Aug. 27, 2015

(51) Int. Cl.
*A23L 1/312* (2006.01)
*A22B 5/00* (2006.01)
*A22B 3/00* (2006.01)
*A23L 1/00* (2006.01)
*A23L 1/03* (2006.01)

(52) U.S. Cl.
CPC .............. *A23L 1/312* (2013.01); *A23L 1/0035* (2013.01); *A23L 1/0345* (2013.01); *A23V 2002/00* (2013.01)

(58) Field of Classification Search
CPC .... A23L 1/312; A23L 1/0017; A22B 5/0005; A22B 3/00

USPC ............................................................ 426/60
See application file for complete search history.

(56) References Cited

U.S. PATENT DOCUMENTS 4,812,444 A * 3/1989 Mitsuhashi ........... A23L 3/3463 127/30

OTHER PUBLICATIONS

CN 1446487 (A)—Machine Translation, English Abstract.*

* cited by examiner

*Primary Examiner* — Hamid R Badr

(57) ABSTRACT

This invention provides a quick and sanitary way to change inedible and almost useless shells of freshwater hard shell turtles into an edible and extremely valuable fermented turtle shell powder with a salutary taste and attractive smell. The novelties taught herein maximize the retention of turtle shell nutrition and minimize any irritation that can be caused from the traditional method of making turtle shell powder. Also, this enhances the digestive absorption of the powder thereby efficiently improving human's health and looks. No negative side effects have been observed to this product. Various steps are provided that enhance the positive benefits of the powder.

14 Claims, 2 Drawing Sheets

US 9,320,296 B2

METHOD OF MAKING FERMENTED TURTLE SHELL POWDER

CROSS-REFERENCE TO RELATED APPLICATIONS

Not Applicable

FIELD OF THE INVENTION

The present invention relates to a process for producing a nutritional powder; more particularly, the present invention relates to a nutritional powder having a primary ingredient, a fermented turtle shell powder that provides various health and medicinal benefits.

BACKGROUND OF THE INVENTION

Turtle shell has been traditionally used in various medicinal compositions for centuries in Chinese herbalism. Though most people view this as being composed of only herbs, Chinese herbalism also includes animals and minerals in addition to the more common plant life ingredients. The traditional Chinese method of preparing a turtle shell powder comprises the following steps as shown in FIG. 1.

Preparation of raw plastron. First, one kills the turtle 1 and then separates the bottom part (plastron) of the hard shell turtle from the carapace by using whatever tools are available 2. To accomplish this, you must also remove the turtle meat 3, and wash the plastron which is the bottom portion of the shell 4; it is subsequently dried in the sun or hung up to dry in the air 5. Because the plastron still has some remaining meat attached, it is soaked in clear water for twenty days during the summer 6, or forty days during the winter 7 without changing water. It is then removed from the basin and washed. Finally, it is dried in the sun 8.

Preparation of vinegar-treated plastron. In this case, completes these additional steps to obtain a satisfactory plastron. First, one places sand in a suitable container such as a pot and heats the pot to a hot enough temperature such that the sand is hot 9. Once the sand is hot enough, a clean raw plastron is placed therein and stir-fry until the plastron turns a golden or yellowish color 10. Next, one removes the sand from the container 11, and places the cooked plastron in a bath of vinegar within another container for a short period of time 12. Then, the plastron is removed from the vinegar bath, washed with water 13, and dried in the sun 14.

Finally, one grinds the vinegar-treated plastron into powder using a particular turtle shell grinding mill 15, and screens out large portions from the fine shell powder using a sieve 16.

However, the traditional manner of making the turtle shell powder has serious deficiencies: (1) the turtle shell powder from the traditional way irritates human's stomach and digestive tract, so people who have digestive tract or stomach problems can definitely NOT eat the turtle shell powder made using the traditional method because it gives them very serious stomach ache; (2) the turtle shell powder made using the traditional method has a very bad smell and tastes awfully preventing people from seeking its medicinal benefits; (3) only the plastron is recommended for use in the traditional method and the carapace is abandoned; (4) the traditional method takes a long time and gives off a very foul smell; (5) the traditional method is not sanitary and safe enough; (6) turtle meat and turtle soup are wasted in the traditional way.

SUMMARY OF THE INVENTION

The present invention overcomes the deficiencies of the known art and the problems that remain unsolved by providing a method of producing a fermented turtle shell powder.

This invention prevents parasitic infections by pretreating a turtle with salt, changing to freshwater for 2-3 weeks, placing the turtle in a container filled with salt water, killing the turtle by heating the container on low heat, boiling the turtle for 5 minutes, opening the turtle shell, removing and disposing of the internal organs but leaving the meat for later use.

This invention improves the taste and smell of the turtle shell powder by boiling the turtle shell and meat along with ginger, red jujube, longan meat, and fructus lycii for 2-3 hours. Also, turtle meat is very easy to be detached from turtle shell to overcome the shortcoming of the traditional way to remove turtle meat. Herein, turtle meat and turtle soup are very delicious, and can be further processed for sell to bring considerably commercial benefits.

This invention greatly reduces water-insoluble mineral salts intake into the powder thereby lowering its potential to irritate the stomach by breaking the turtle shell into small pieces and soaking the small pieces in vinegar for 3 hours.

This invention enhances the digestive absorption of the powder and minimizes the irritation that can be caused from the traditional method of making turtle shell powder by mixing a turtle shell powder with a carbohydrate and fermenting the mixture with microorganisms for a period of time.

A fermented turtle shell powder comprises a fermented turtle shell powder and a carbohydrate.

BRIEF DESCRIPTION OF THE DRAWINGS

A comparison between the traditional method and the invention is described in the appended drawings.

DETAILED DESCRIPTION OF THE INVENTION

The various steps utilized in the process of preparing a fermented turtle shell powder are described below. More particularly, for a wild turtle with a carapace length of no less than 4 inches, follow steps 1 to 15; for a farm raised live turtle with a carapace length of no less than 4 inches, follow steps 3 to 15; for a dead market bought turtle, follow steps 6 to 15; finally, for a turtle shell bought from a company or a discarded turtle shell, follow steps 7 to 15.

Figure 1:
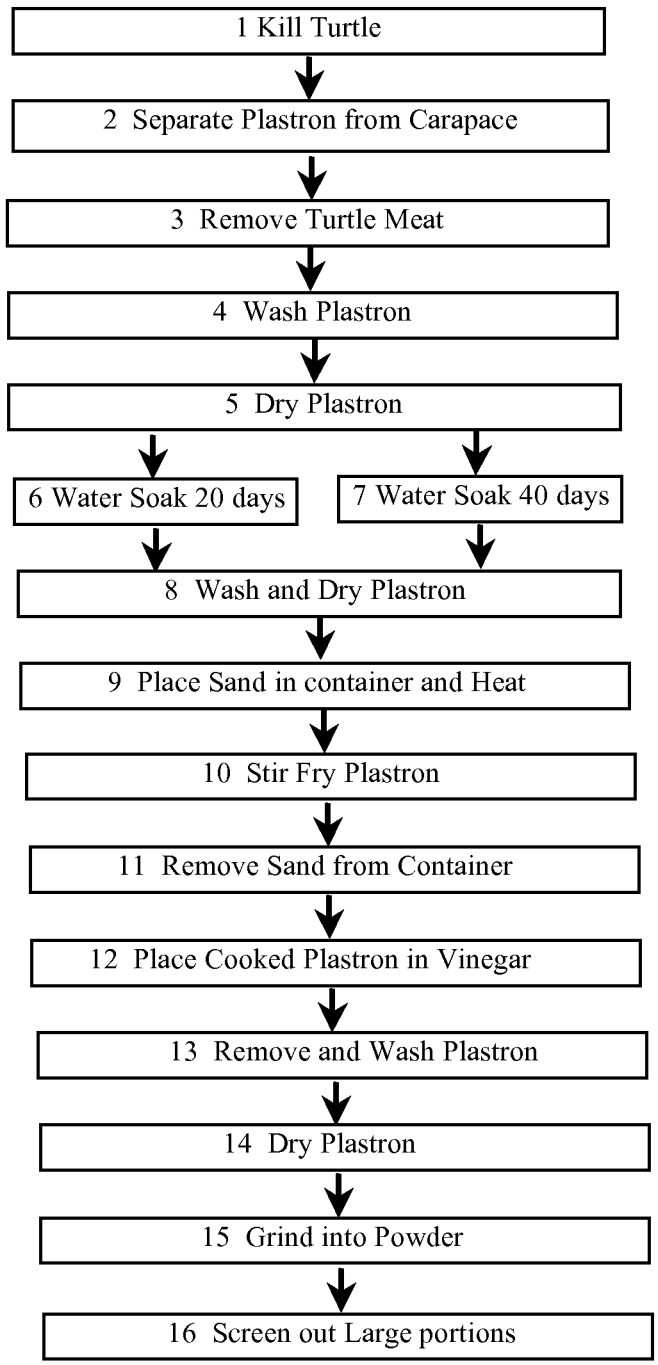
FIG. 1 depicts the prior art of making a turtle shell powder.
Figure 2:
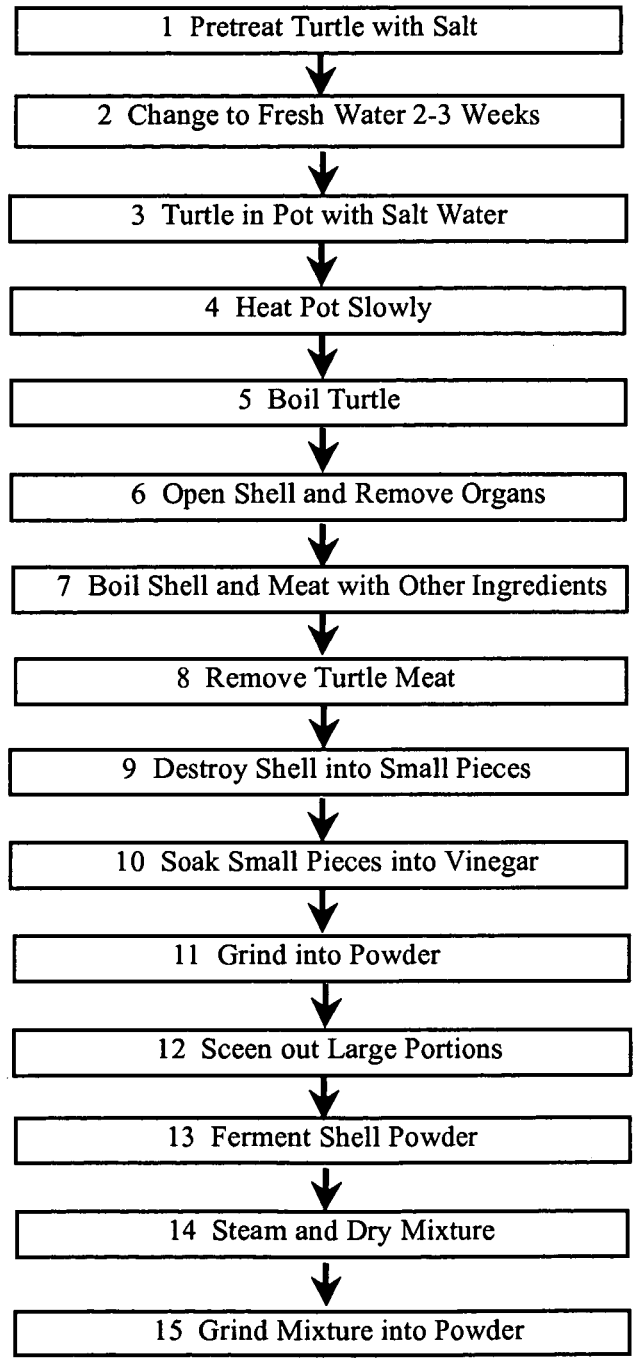
FIG. 2 depicts the process of producing a fermented turtle shell powder of the invention.

FIG. 2 depicts the process of producing a fermented turtle shell powder of the invention.

1. First, since a freshwater hard shell wild turtle carries a lot of parasites, a lot of salt should be added outside of its body and it should be left in salt for 2-5 hours to kill most if not all parasites.

2. Place the turtle in clear water for 2-3 weeks, changing to the fresh water every day to clear most of the turtle excrement; it should be understood that no food is given to the turtle.

3. After this, place the turtle in a pot, add a lot of salt and enough water to immerse the turtle completely therein.

4. Heat the pot on low heat slowly increasing the temperature thereby clearing any and all parasites and excrement in its body; as soon as the temperature is high enough, the turtle will be killed.

5. Heating continues on high heat and temperature is rapidly increasing in the pot. As a result, the turtle body is boiled for 5 minutes.

6. Next, one hammers the turtle shell to open it, and removes all internal organs but keeps the meat for later use. Wash the turtle shell and meat for 3 times.

7. Boil the turtle shell in a pot of water along with the turtle meat as well as some ginger, red jujube, longan meat, and fructus lycii for 2-3 hours. For example, a four-pound turtle needs 40-120 grams of ginger, 50-150 grams of red jujube, 50-150 grams of longan meat, 50-150 grams of fructus lycii.

8. Take the shell (both carapace and plastron) out of the pot, wash with water, and remove all meat from the shell, then dry the turtle shell by heating in a stove at 200° F. for 3 hours.

9. Next, a user destroys the turtle shell into 1 cm size pieces by a grinding mill or a hammer.

10. Then, one soaks the shell pieces in a container of vinegar for 3 hours.

11. Take the shell pieces out of vinegar, wash 3 times by water, and dry in a oven at 200° F. or by a vacuum, then grind the shell pieces into powder by a grinding mill such as a coffee grinder.

12. Screen out large portions from the fine shell powder using a sieve. Regrind the large portions and screen again using a sieve. Repeat grinding and screening until almost all the large portions are grinded into the fine shell powder.

13. Mix the turtle shell powder in a container with a carbohydrate; then ferment with microorganisms, which are yeasts, bacteria, molds, or a combination thereof, for a period of time. The preferred embodiment to perform this step is as follows:

Mix the turtle shell powder in a container with flour by volume ratio 1:1, then add 1.0-1.2 volume of water containing 0.5-5% yeast powder, 1-20% sugar, mix well, then ferment at 68-131° F. (preferably 80-100° F.) for 12 hours-30 days (preferably 24-48 hours). Herein, the ratio of turtle shell powder to flour can be adjusted to fit the needs of different people.

14. Next, steam the mixture for 20-30 min, then dry by a vacuum or heating in a stove at 200° F.

15. A user then grinds the mixture into powder by a grinding mill such as a coffee grinder, similar mechanical grinder or manual grinding. Pick out extra-large portions. Herein, the turtle shell powder tablet or pill can be made.

The final mixture should be taken by mouth 3-5 grams per day by putting the powder into the mouth, chewing it, and swallowing it with water preferably at night before going to bed.

Medicinal Benefits of the Fermented Turtle Shell Powder

The wild type red-eared slider turtles with a carapace length of no less than 4 inches (preferably no less than 9 inches) have been utilized to make the fermented turtle shell powder to test their medicinal benefits to humans. Red-eared sliders are the most commonly traded turtles in the world. No side effects have been observed. Some users indicated that they observed obvious positive effects within 24 hours of the first dose of the fermented turtle shell powder mixture. By now, these medicinal benefits have been observed with the fermented turtle powder mixture: (1) making people much more energetic and clear-minded; (2) improving human looks by improving skin tone; (3) improving ability to resist cold and inhibiting Raynaud's disease; (4) optimizing blood pressure and heart rate; (5) inhibiting back pain; (6) improving sleep quality; (7) improving kidney function and urination; (8) improving hearing and inhibiting tinnitus; (9) inhibiting nasal inflammation; (10) inhibiting constipation; (11) improving men's sex function and increasing sexual desire.

Herein, a typical case is provided to further illustrate the medicinal effects of the fermented turtle shell powder of the invention. Amruta Mhashilkar, M.D., has a Post Graduate Diploma in Clinical Research, a National Certification in Public Health and a Master in Public Health. Before she took the turtle powder, her diastolic pressure was 105 mmHg, systolic pressure was 120 mmHg, and heart rate was 96 beats per minute. She had Raynaud's disease, so cold temperature was detrimental to her vasculature. She got cyanosed easily. She had a very poor tolerance to cold as she got frequent vasospasms. She used to feel very tired. She took the turtle powder 3-5 grams on Dec. 16, 2013. Within an hour of eating the powder, she felt heat in her stomach. Then her muscles got more blood supply. She felt the blood rushing in muscles, which was good to her right leg that had compromised blood flow. She felt her heart was very comfortable and heart rate was stable. After 2 hours of eating the turtle powder, she suddenly felt a lot energetic and she was not feeling tired anymore. She felt like her metabolism had increased. The status of being much energetic and clear-minded could keep a few days by one dose of the turtle powder. From the day she ate the turtle powder, her ability to resist cold greatly improved and she could withstand great deal of low temperature. Her heart rate and blood pressure began to optimize from the second day of eating the turtle powder. After 10 days of eating the turtle powder, her diastolic pressure was 78 mmHg, systolic pressure was 110 mmHg, and heart rate was 78 beats per minute. Her facial skin condition began to improve from Dec. 23, 2013. By two weeks of turtle powder, her facial skin was much more smooth and shining than ever before. Also, she looked younger and had better looks than before. She testified that the taste of the powder was very faintly sweet; it was crunchy and could be chewed; there was no odor to it; it didn't smell bad at all; it was easy to eat and swallow; it did not leave any bad taste in mouth; no pungent feeling; the turtle powder had no side effects to her.

Taking the fermented turtle shell powder of this invention is highly beneficial to the health of the people who have deficiencies in kidney, blood and heart.

Various Differences Over the Traditional Method

1. Both parts of the turtle shell are used in this novel method; i.e., the carapace and the plastron of the turtle shell are used as taught herein. Only the plastron is recommended for use in the traditional method.

2. The invention provides a sanitary, quick and convenient way of preparing turtle shell that has no unpleasant odor. The traditional method takes a long time and gives off a very foul smell.

3. The embodiments as taught absolutely exclude all possibilities of parasitic infections by pretreating a turtle with salt, changing to freshwater for 2-3 weeks, killing the turtle by heating the pot on low heat, removing all its internal organs, boiling the turtle shell for 2-3 hours, and drying the shell in oven for 3 hours.

4. This method is safe and sanitary for people as the turtle is killed by heat. The traditional way of killing the turtle by decapitation is dangerous and unsanitary.

5. Also, boiling the turtle shell, turtle meat along with some ginger, red jujube, longan meat, and fructus lycii for 2-3 hours improves the taste and smell of the turtle shell powder; this renders the turtle meat and turtle soup edible by humans thereby efficiently using all natural resources. The traditional turtle shell powder tastes and smells badly. The turtle meat and turtle soup are wasted in the traditional way.

6. This method soaks the turtle shell pieces in vinegar for 3 hours instead of the whole plastron in vinegar for a little while, which is recommended in the traditional way. This invention greatly reduces water-insoluble mineral salts intake into the powder thereby lowering its potential to irritate the stomach. It should be understood that turtle shell powder from traditional way irritates human's stomach and digestive tract and this new method overcomes that problem.

7. Mixing of a turtle shell powder with a carbohydrate feed as well as fermenting for a period of time modifies the turtle shell powder by microorganisms reacting; this has the concomitant effect of helping human's digestive absorption of the turtle shell powder. This step minimizes and even gets rid of any residual irritation that might have been caused by a turtle shell powder to the stomach and digestive tract without this step; thus, people who have digestive tract or stomach problem can eat the fermented turtle shell powder without fearing any unpleasant side effects. On the other hand, people who have digestive tract or stomach problems can definitely NOT eat the turtle shell powder made using the traditional method because it gives them very serious stomach ache.

8. The fermented turtle shell powder has a very good smell, and tastes just like biscuits or a dessert. In contrast, the turtle shell powder made using the traditional method has a very bad smell and tastes awfully preventing people from seeking its medicinal benefits.

9. Next, the turtle shell powder prepared from the traditional way doesn't solve the digestive absorption issue, and it is therefore not good for long-term use. This novel method solves the digestive absorption issue, so it is good for long-term use.

10. The wild type red-eared sliders with a carapace length of no less than 4 inches (preferably no less than 9 inches) have been utilized to make the fermented turtle shell powder to test their medicinal benefits to humans. Red-eared slider turtles are the most commonly traded turtles in the world. This is the first attempt to make turtle shell powder from red-eared sliders, and is the first to show that red-eared slider turtles in fact do have important medicinal value.

11. Our initial tests show that the fermented turtle shell powder from step 15 provides no less positive medicinal benefits than equal amount of the turtle shell powder from step 12. That means this invention saves about half amount of turtle shells from mixing the turtle shell powder with flour by 1 to 1 volume ratio.

What is claimed is:

1. A method of producing a fermented turtle shell powder, comprising the steps of:
   a. breaking a turtle shell into small pieces;
   b. soaking the small pieces in vinegar for 3 hours;
   c. washing and drying the vinegar treated small pieces;
   d. grinding the dried small pieces to produce a fine shell powder and coarse pieces;
   e. mixing the fine shell powder with carbohydrates and fermenting it for a period of time.

2. The method of claim 1 wherein the fermenting is done by yeast.

3. The method of claim 1 wherein the turtle shell is obtained by a process comprising:
   f. pretreating a turtle with salt;
   g. soaking the salt treated turtle in freshwater and changing the water for 2-3 weeks;
   h. placing the pretreated turtle in a container filled with salt water;
   i. killing the turtle by heating the container on low heat;
   j. boiling the turtle for 5 minutes; and
   k. opening the turtle shell, removing and disposing of organs leaving the meat for later use.

4. The method of claim 2, further comprising the step of:
   l. boiling the turtle shell and meat along with other ingredients selected from the group consisting of ginger, red jujube, longan meat, fructus lycii and combinations thereof for 2-3 hours.

5. The method of claim 3 wherein one of the other ingredients is ginger.

6. The method of claim 3 wherein one of the other ingredients is red jujube.

7. The method of claim 3 wherein one of the other ingredients is longan meat.

8. The method of claim 3 wherein one of the other ingredients is fructus lycii.

9. The method of claim 3 wherein the other ingredients are a combination of ginger, red jujube, longan meat and fructus lycii.

10. The method of claim 8, further comprising the step of:
    m. removing all turtle meat from the shell and drying the shell with heat.

11. The method of claim 1, further comprising the step of:
    n. separating the fine shell powder from coarse pieces.

12. The method of claim 1, further comprising steaming and drying the fermented turtle shell.

13. The method of claim 1, further comprising grinding the fermented turtle shell into a powder.

14. A fermented turtle shell powder produced according to claim 1.

* * * * *

UNITED STATES PATENT AND TRADEMARK OFFICE
CERTIFICATE OF CORRECTION

PATENT NO. : 9,320,296 B2
APPLICATION NO. : 14/187779
DATED : April 26, 2016
INVENTOR(S) : Canhui Liu It is certified that error appears in the above-identified patent and that said Letters Patent is hereby corrected as shown below:

In the Specification

Column 1,
line 46, replace "into powder" with -- into a powder --

Column 2,
lines 24-25, delete the entire paragraph "A fermented turtle shell powder comprises a fermented turtle shell powder and a carbohydrate."
lines 56-57, replace "slowly increasing the temperature" with -- to increase the temperature slowly --

Column 3,
line 6, replace "in a stove" with -- in an oven --
line 12, replace "in a oven" with -- in an oven --
line 13, replace "into powder" with -- into a powder --
line 31, replace "in a stove" with -- in an oven --
line 32, replace "into powder" with -- into a powder --
line 48, replace "turtle shell powder mixture" with -- turtle shell powder --
line 50, replace "turtle powder mixture" with -- turtle shell powder --

Column 4,
line 37, replace "turtle shell" with -- a turtle shell --
line 45, replace "oven" with -- an oven --
line 61, replace "turtle shell" with -- the turtle shell --
line 64, replace "a carbohydrate feed" with -- a carbohydrate --

Column 5,
line 25, replace "turtle shell" with -- a turtle shell --

Signed and Sealed this
Twenty-eighth Day of June, 2016

Michelle K. Lee
*Director of the United States Patent and Trademark Office*

In the Claims

Column 6,
lines 14-32, replace claims 4-10 with the following:

-- 4. The method of claim 3, further comprising the step of: l. boiling the turtle shell and meat along with other ingredients selected from the group consisting of ginger, red jujube, longan meat, fructus lycii and combinations thereof for 2-3 hours.
5. The method of claim 4 wherein one of the other ingredients is ginger.
6. The method of claim 4 wherein one of the other ingredients is red jujube.
7. The method of claim 4 wherein one of the other ingredients is longan meat.
8. The method of claim 4 wherein one of the other ingredients is fructus lycii.
9. The method of claim 4 wherein the other ingredients are a combination of ginger, red jujube, longan meat and fructus lycii.
10. The method of claim 9, further comprising the step of: m. removing all turtle meat from the shell and drying the shell with heat. --